(12) United States Patent
Buddharaju

(10) Patent No.: US 8,430,098 B1
(45) Date of Patent: Apr. 30, 2013

(54) STRAPLESS NASAL INTERFACE DEVICE

(76) Inventor: Venkata Buddharaju, Park Ridge, IL (US)

( * ) Notice: Subject to any disclaimer, the term of this patent is extended or adjusted under 35 U.S.C. 154(b) by 480 days.

(21) Appl. No.: 12/641,094

(22) Filed: Dec. 17, 2009

Related U.S. Application Data

(60) Provisional application No. 61/138,472, filed on Dec. 17, 2008.

(51) Int. Cl.
*A61M 16/00* (2006.01)
*A61M 15/08* (2006.01)
*A62B 7/00* (2006.01)

(52) U.S. Cl.
USPC .............................. 128/204.18; 128/207.18

(58) Field of Classification Search ............ 128/206.25, 128/206.21, 207.13, 207.18, 200.26, 203.22, 128/206.11, 204.18–205.25
See application file for complete search history.

(56) References Cited

U.S. PATENT DOCUMENTS

| | | | |
|---|---|---|---|
| 3,288,136 A * | 11/1966 | Lund ............................. | 604/180 |
| 4,660,555 A * | 4/1987 | Payton ..................... | 128/207.18 |
| 4,932,943 A * | 6/1990 | Nowak .......................... | 604/180 |
| 5,535,739 A * | 7/1996 | Rapoport et al. ........ | 128/204.23 |
| 5,806,525 A | 9/1998 | Pope, Jr. | |
| 6,183,493 B1 | 2/2001 | Zammit | |
| 6,405,729 B1 * | 6/2002 | Thornton ..................... | 128/848 |
| 6,478,026 B1 | 11/2002 | Wood | |
| 6,571,798 B1 | 6/2003 | Thornton | |
| 6,581,594 B1 | 6/2003 | Drew et al. | |
| 6,595,215 B2 | 7/2003 | Wood | |
| 6,776,162 B2 | 8/2004 | Wood | |
| 6,863,069 B2 | 3/2005 | Wood | |
| 6,994,089 B2 | 2/2006 | Wood | |
| 6,997,187 B2 | 2/2006 | Wood | |
| 7,000,613 B2 | 2/2006 | Wood | |
| 7,234,465 B2 | 6/2007 | Wood | |
| 2004/0182377 A1 | 9/2004 | Johnsson et al. | |
| 2005/0252515 A1 | 11/2005 | Wood et al. | |
| 2005/0284479 A1 | 12/2005 | Schrader et al. | |
| 2006/0196509 A1 | 9/2006 | Drew et al. | |
| 2007/0000492 A1 | 1/2007 | Hansel et al. | |
| 2007/0125387 A1 | 6/2007 | Zollinger et al. | |
| 2007/0272249 A1 | 11/2007 | Chandran et al. | |
| 2008/0011305 A1 | 1/2008 | Chandran et al. | |

(Continued)

*Primary Examiner* — Laura A Bouchelle
*Assistant Examiner* — Leah Stohr
(74) *Attorney, Agent, or Firm* — Michael Best & Friedrich LLP

(57) ABSTRACT

A strapless nasal interface device is disclosed. The device is used in conjunction with CPAP, BIPAP, ventilators, or any other suitable device. The device includes a body with a passageway to a ventilating tube, exhalation holes, and a passageway to nostril interface tubes. The nostril interface tubes include a nasal interface element which is an expandable, compressible material such that the user can compress the element, insert it into the end of the nostril and allow it to expand to hold the tube in place. Alternatively, the nasal interface elements are held against the outer edge of the nostrils. Optionally, a skirt is included at the outer side of the nostril to aid in sealing against air leaks. Optionally, flaps are included to assist in holding the device in place, such as side flaps, a front flap, or both. The front flap may be adherable to the exterior of the nose and optionally includes resilient strips to open the nasal passageway. Alternatively, a nose cover is adhered to the nose and side attachment flaps secure the device to the nose cover. Thus, the device requires no additional straps or headgear in order to maintain the device in operable position during sleep.

20 Claims, 4 Drawing Sheets

U.S. PATENT DOCUMENTS

| | | |
|---|---|---|
| 2008/0264421 A1 | 10/2008 | Kwok et al. |
| 2008/0295846 A1 | 12/2008 | Han et al. |
| 2008/0302365 A1 | 12/2008 | Cohen et al. |
| 2009/0107507 A1 | 4/2009 | Moore |
| 2009/0139525 A1 | 6/2009 | Schirm |
| 2009/0308398 A1 | 12/2009 | Ferdinand et al. |
| 2010/0037897 A1 | 2/2010 | Wood |
| 2010/0258128 A1 | 10/2010 | Zollinger et al. |
| 2011/0011397 A1 | 1/2011 | Ziv et al. |

* cited by examiner

STRAPLESS NASAL INTERFACE DEVICE

CROSS-REFERENCE TO RELATED APPLICATIONS

This application claims the benefit of U.S. Provisional Application No. 61/138,472, filed Dec. 17, 2008, which is hereby incorporated by reference herein in its entirety.

BACKGROUND OF THE INVENTION

1. Field of the Invention

The present invention relates to a strapless nasal interface device, and more particularly, to a device for use with a ventilator, CPAP, or BIPAP for strapless interface with the nasal passages.

2. Background

Nasal passage interface devices are commonly used in conjunction with CPAP devices, BIPAP, ventilators, and other devices. For example, in CPAP applications, a nasal passage interface device is used to provide a passageway for air to enter the nasal passages of the user. Such devices must be secured to the nasal passages so that it remains in place during sleep.

Various existing interfaces are typically held in place by straps or headgear. Such straps can become uncomfortable to the user, and can deter use of the device. Thus, existing devices are deficient in that they fail to provide an ideal method of attachment.

Numerous such interfaces have been disclosed. For example, U.S. Pat. No. 6,405,729, issued to Thornton, discloses an oral appliance for improving breathing. The appliance includes a mouthpiece and two nasal cushions which sit on the outside of the nose. The device requires the use of the mouthpiece to hold it in place, which would be uncomfortable for a user not in need of the mouthpiece. Without the mouthpiece, the nasal interface would not hold the unit in place.

U.S. Pat. No. 6,478,026, issued to Wood, discloses a nasal ventilation interface. The unit includes tubes which insert into the nose of the user. However, the inserts do not hold the unit in place. The devices requires that the air tubes be looped over the ears of the user to hold the unit in place, which would be uncomfortable and easily dislodged during sleep.

Another device is disclosed in U.S. Pat. No. 6,581,594, issued to Drew et al. In this patent, a cumbersome respiratory mask is disclosed which covers the nose of the user. A forehead piece extends from the unit and is attachable to straps to hold the unit in place. The device is rather obtrusive and would have both straps to hold the device in place and a mask, both of which would be uncomfortable for a user.

Yet another device is disclosed in U.S. Pat. No. 7,000,613, issued to Wood et al. In this patent, an interface device also has tubes which extend into the nasal passage. Again, straps in the form of head straps are used to secure the device, which can cause discomfort to a user.

In U.S. Published Patent Application No. 2004/0182397, filed by Wood, a ventilation interface is disclosed having tubes extending into the nares of the nose. In this disclosure, seal portions inserted into the nostrils are disclosed. However, these seal portions are not capable of securing the device to the user, and thus, further securing methods such as straps are needed, again causing potential discomfort to the user.

Another typical interface device is disclosed in U.S. Published Patent Application No. 2007/0272249, filed by Chandran et al. In this device, pillows are included which wedge into the nares of the nose. However, again, these pillows do not secure the device, and straps of various sorts would be required to hold it in place.

While a number of other interface devices have been used or disclosed, none of them enable securing via nasal inserts to eliminate the use of straps or air tube contraptions to secure the device to the user's nose. Furthermore, they each pose a level of potential discomfort to the user which render them problematic for sleeping.

Thus, there continues to be a need for a particular suitable nasal passage interface device which can be secured without the need for straps or air tube arrangements, and which provides a greater comfort level to the user.

SUMMARY

The present invention is a strapless nasal interface device for use with a CPAP or BIPAP device, or any other ventilator type device. The nasal interface device of the present invention enables the user to secure the device in place without the need for straps or headgear, which can be uncomfortable for the user. Typical PAP devices are secured to the user via straps which wrap around the head of the user. These straps can be very uncomfortable, and can even deter use of the device altogether. Straps can be particularly uncomfortable when the head is tilted in various directions during sleep. This problem may also be particularly present in patients having claustrophobia issues when headgear or straps can be perceived as enclosing on a patient. Additionally, eliminating straps or headgear can make the maintenance and cleaning of the device easier. Providing a lightweight device which can be secured without straps or headgear is thus most advantageous.

The nasal interface device of the present invention includes an interface body which is preferably light weight and low profile. A ventilation tube is connected to the body, such as a tube through which air is supplied via a CPAP or other device. The body also includes exhalation holes. Thus, when the user exhales, the carbon dioxide rich exhalation air can exit through the exhalation holes, allowing new air to enter.

The body of the device interfaces with the nasal passage via nostril interface tubes extending from the body. These tubes include a nasal interface element designed to aid in securing the device in place, and thus eliminating the need for straps or headgear. The nasal interface elements are formed of an expandable, compressible material, meaning they can be compressed in order to insert them into the nostril, and once inserted they expand to apply pressure to the inner surfaces of the nostril opening to hold the device in place. Preferably, the contact is made at the end portion of the nostril so that only the section in the nostril covered by skin is contacted, thus avoiding the more sensitive nasal mucosa. Alternatively, the nostril interface elements are held against the outer edge of the nostrils.

These nasal interface elements can be formed of any suitable material which can be deformed, but are resilient in that they tend back to their original shape. A compressible foam is one material which may be well-suited for use in the invention. The interface element can be either permanently mounted to the interface tubes, or they may be removable and disposable so that they can be replaced after use. Thus, they can be mounted to the tubes via any suitable method. For example, they can be mounted via threading, frictional fit, or adhesive. However, other suitable methods of mounting the element to the tubes are contemplated and considered within the scope of the present invention.

The nasal interface elements of the present invention are ideally shaped in such a manner that they will form a seal or snug fit within the nostril of the user. This may mean they have more material on the bottom part toward the user's face, or that they may be specially formed to conform to the shape of the interior of the nostril. By exerting a small amount of pressure to the inside of the nostril, an additional advantage can be obtained by widening the passageway to allow more airflow. Furthermore, to enhance the securing of the device, the interface elements may include a mild adhesive on their exterior surface to hold them in place against the inner surfaces of the nostril. Such adhesive must be mild enough that the element can be easily removed by the user without causing significant discomfort or irritation or abrasion.

Optionally, these interface elements may contain an antibacterial agent to reduce the growth of contaminants. Once used, the user may replace the elements onto the tubes.

In various embodiments of the present invention, the interface tubes may further include a skirt surrounding the tube below the interface elements. Such skirts can be fitted against the outside of the nostril opening to help form a seal. Optionally, a mild adhesive can be disposed on the surface of the skirt which touches the outside edge of the nasal opening to help hold it in place.

In various embodiments of the present invention, the device also includes one or more flaps to assist in holding the device in place while in use. For example, side flaps are optionally included extending from the sides of the body of the device. The side flaps have an adhesive, enabling them to be adhered to the outer surface of the nose of the user to secure the device in place. Alternatively, the side flaps may removably secure to a nose cover which is adhered to the nose of the user.

Furthermore, an optional front flap may be included. The front flap extends from the body of the device and is secured to the exterior surface of the nose of the user. It may be secured via a strip of tape, and adhesive on the underside of the flap, or by any other suitable method. This front flap holds the device in place during use. In certain embodiments, the front flap may include resilient strips traversing the exterior of the nasal passageways. These strips can be deformed when applying the front flap to the nose via an adhesive, and will apply pressure tending to open the nasal passageways. A single one of such strips can be used. Alternatively, multiple strips can be used. Thus, the passageway is opened to allow more airflow, reducing the tendency of snoring in the user, and potentially reducing the air pressure required through the device to accomplish its purpose. Greater airflow may be enhanced by the combination of the strips and the expanding nasal interface elements, thus reducing air pressure requirements.

Still other objects and advantages of the present invention will become readily apparent to those skilled in the art from the following detailed description, wherein it is shown and described only the preferred embodiments of the invention, simply by way of illustration of the best mode contemplated of carrying out the invention. As will be realized, the invention is capable of other and different embodiments and its several details are capable of modifications in various obvious respects, without departing from the invention. Accordingly, the drawings, wherein like reference numerals represent like features, and description are to be regarded as illustrative in nature and not as restrictive.

DETAILED DESCRIPTION OF THE INVENTION

Figure 1:
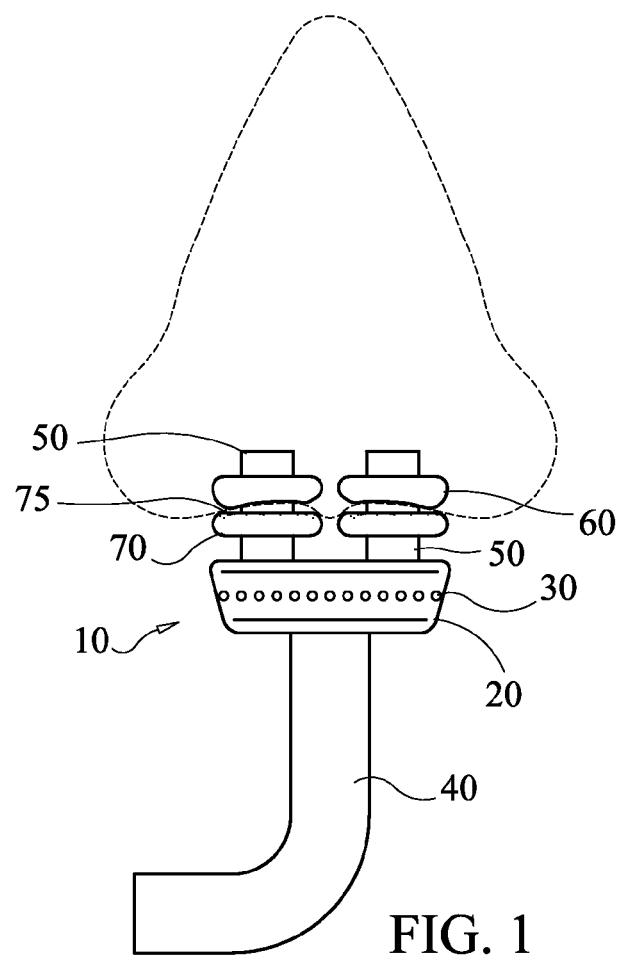
FIG. 1 shows an embodiment of the nasal interface device of the present invention.
Figure 2:
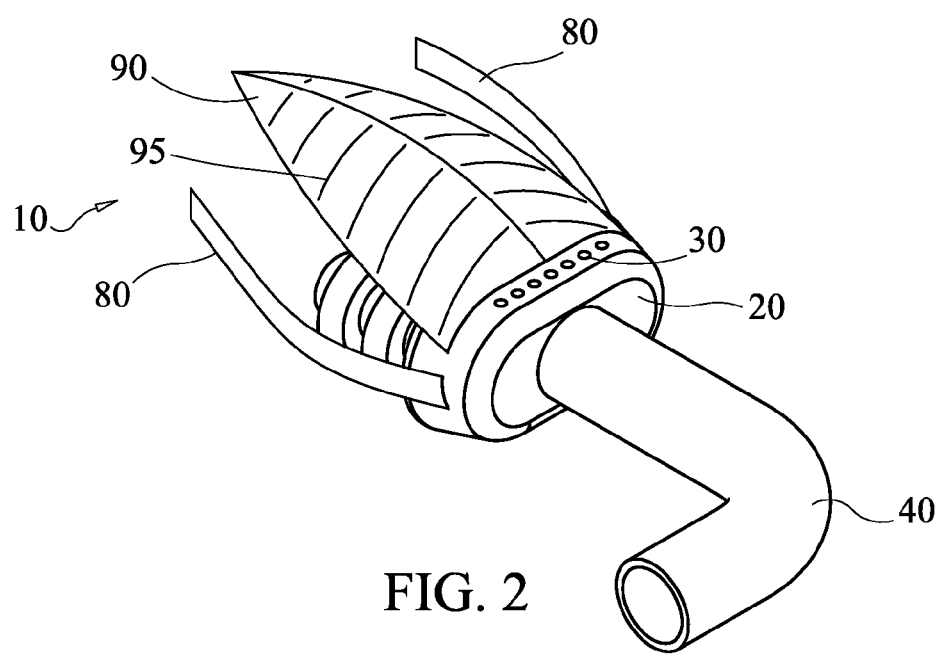
FIG. 2 shows another embodiment of the nasal interface device of the present invention, having optional side and front straps for mounting the device.
Figure 3:
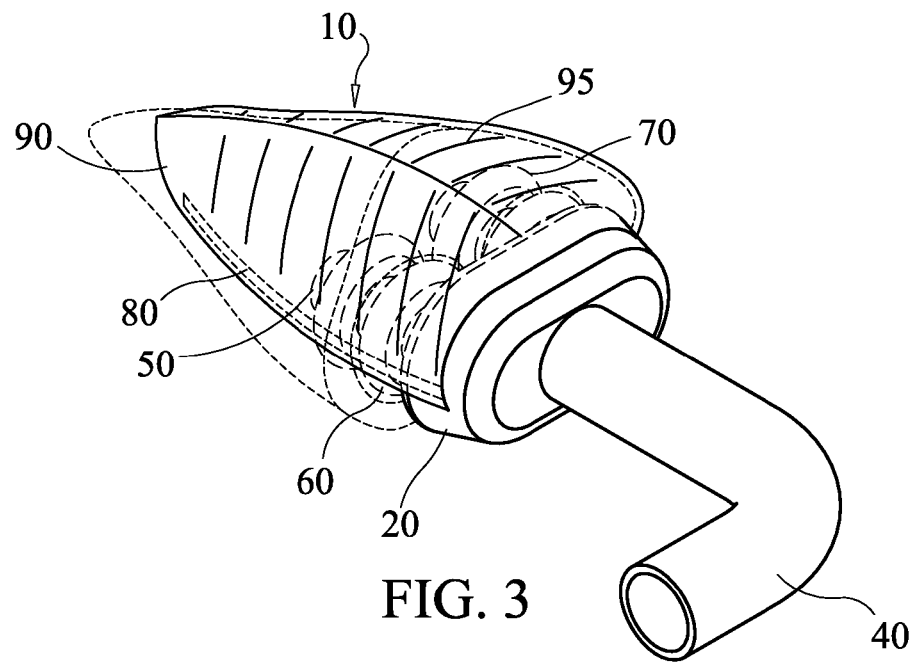
FIG. 3 shows an embodiment of the nasal interface device of the present invention as mounted on the nose of a user.
Figure 4:
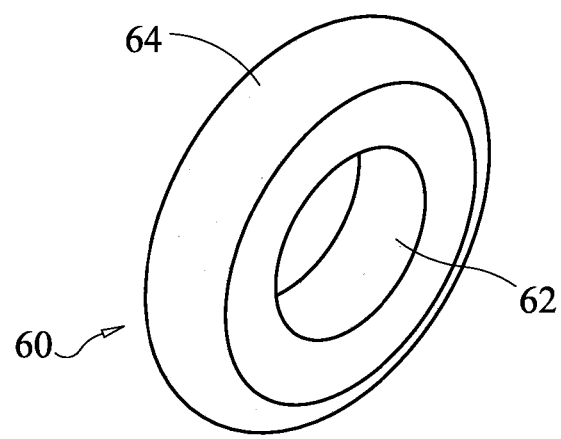
FIG. 4 shows an embodiment of the nasal interface element of the present invention.
Figure 5:
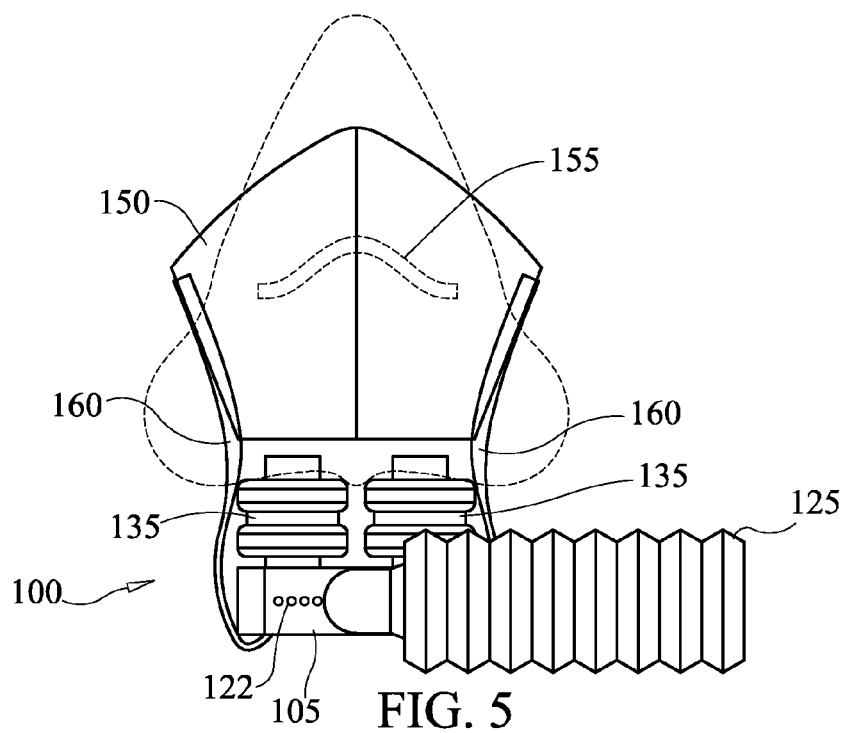
FIG. 5 shows another embodiment of the nasal interface device of the present invention.
Figure 6:
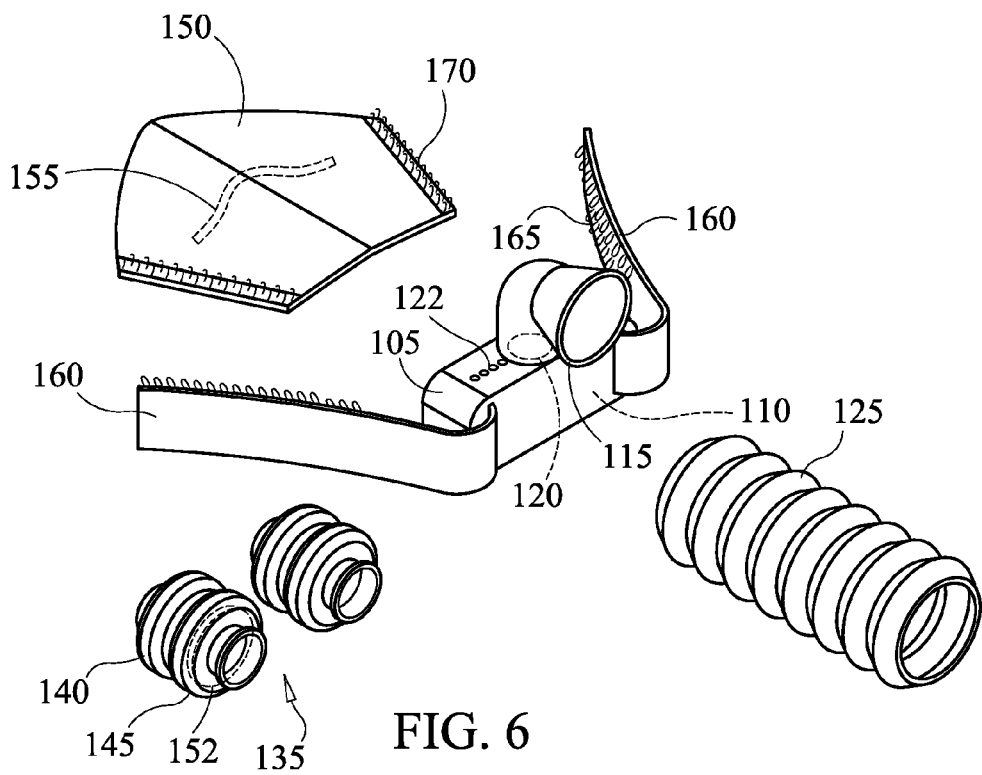
FIG. 6 shows an exploded view of one embodiment of the nasal interface device of the present invention.
Figure 7:
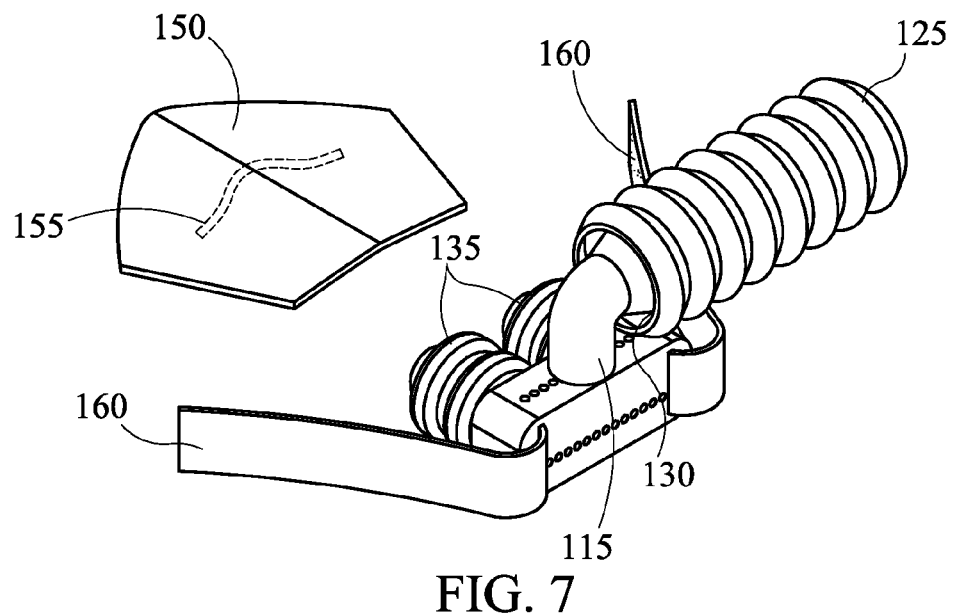
FIG. 7 shows a perspective view of one embodiment of the nasal interface device of the present invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

The present invention is a strapless nasal interface device 10 suitable for use with a CPAP or BIPAP device, or any other ventilator type device. The device 10 includes an interface body 20 having an interior cavity. The cavity is fluidly connected to an air tube 40 extending from the body 20 for use with a CPAP or other device. The body 20 ideally includes exhalation holes 30 to enable expelled air to escape the device 10.

The device 10 further includes at least one nostril interface tube 50 extending from the body 20 to interface with the nasal passages of the user. Preferably, two such tubes 50 are included. Surrounding the tubes are compressible expandable nasal interface elements 60. These elements 60 are formed such that they can be compressed to fit within the nostril of the user, after which they expand to make contact with the interior of the nostril at the inner edge of the nostril to hold the interface tube 50 in place within the nostril. Thus, the need for straps or headgear in conjunction with the device is eliminated.

In various embodiments of the present invention, the interface elements 60 are permanently mounted to the interface tubes 50. However, in various other embodiments, the interface elements 60 are removably mounted to the tubes 50. If removably mounted, the interface elements 60 may be mounted to the tubes 50 by any suitable means. For example, they may be threaded, frictionally fit, or adhered with an adhesive 62.

Interface elements 60 can be formed of any suitable material. In certain embodiments, they are formed of an expandable, compressible foam. Preferably, the elements 60 have an anti-bacterial agent. Optionally, elements 60 may include a mild adhesive 64 on the outer surface to make contact with the skin on the interior of the nostril. Ideally, elements 60 form a seal within the nostril. Ideally, they are shaped to optimize such a seal. For example, they may be formed to conform to the interior shape of the nostril so as to form a proper fit.

In various embodiments of the present invention, a skirt 70 is also included. The skirt 70 is disposed on the nostril interface tube 50 between the interface element 60 and the interface body 20. The skirt interfaces with the end of the nostril opening to help aid in sealing the air passage. Optionally, a mild adhesive can be disposed on the surface 75 of the skirt 70 adjacent the rim of the nostril opening to further seal the passageway.

In various further embodiments, the device 10 includes one or more flaps in order to further secure it on the user. For example, in certain embodiments, side flaps 80 extend from the body 20. The side flaps 80 have an adhesive thereon to adhere the flaps to the exterior of the nose, further securing it. Side flaps 80 may be mounted to the interface body 20 by any suitable method, such as via a groove in the interface body 20 allowing an end of flap 20 to be inserted. Such a fit may be a friction fit, or it may be a dovetail groove. However, any other suitable method of attachment is contemplated as within the scope of the invention.

Additionally, an optional front flap 90 may extend from the interface body 20. The front flap 90 covers an exterior portion of the nose. It can be mounted to the nose via any suitable method. For example, a separate strip of tape or adhesive may be used. In certain embodiments, it may be mounted via an adhesive on the underside of the front flap 90. Thus, the device 10 is further secured to the nose of the user. Front flap 90 may be mounted to the interface body 20 by any suitable method, such as via a groove in the interface body 20 allowing an end of flap 90 to be inserted. Such a fit may be a friction fit, or it may be a dovetail groove. However, any other suitable method of attachment is contemplated as within the scope of the invention.

In various embodiments, the front flap 90 of the device 10 further includes tension bows or strips 95. These strips 95 are formed of a resilient material. Thus, the strips 95 may be deformed when adhered to the exterior of the nose via an adhesive on the underside of the front flap 90, after which they apply pressure tending to expand the nasal passageway. Thus, the passageways are expanded, relieving a tendency of snoring and potentially reducing the air pressure required for the user's purposes. While a single such strip 95 can be used, in certain embodiments multiple strips 95 are used to open the passageway along an entire portion of the passageway. The front flap 90 can be used without side flaps 80, or in conjunction therewith.

In various other embodiments, the present invention includes a strapless nasal interface device 100 having an interface body 105 having an internal cavity 110. The cavity 110 is in communication with an air tube 115 which extends from the body 105. The air tube 115 is preferably rotatably attached to the interface body 105 at a first point of attachment 120. Ideally, this point of attachment 120 allows the air tube 115 to rotate 360 degrees, yet maintains a substantially leak-proof connection regardless of how the air tube 115 is oriented with respect to the interface body 105. A sealing o-ring may be incorporated to facilitate the rotatable mounting. This first point of attachment 120 may be located at any suitable position on interface body 105, however, in a preferred embodiment it is located on a front wall which is adjacent the wall on which nostril interface tubes 135 are located such that the air tube 115 extends out perpendicular to the plane of the face and away from the face, thus keeping air tube 115 and air supply tube 125 from rubbing against the face of the user.

Preferably, the device 100 comprises at least one exhalation hole, and preferably a plurality of exhalation ports or holes 122 which are sized to allow exhaled air to pass therethrough, but which are sized so that they do not substantially depressurize the cavity 110 of the interface body 105. Exhalation holes 122 can be placed in any suitable location on the interface body 105. For example, they may be placed on the side opposite of where nostril interface tubes 135 are located, or on the top side of the interface body 105 near the first point of attachment 120, or in both locations, or in any other suitable location. In certain embodiments, 35 to 40 exhalation holes sized at about 0.023 inches each may be suitable to enable carbon dioxide rich exhalation air to leave the cavity 110, yet such holes 122 are small enough such that air pressure intended to pressurize the nasal passage is maintained. In another embodiment, hole sizes may be approximately 0.02 inches in diameter, and about 78 of them may be suitable. However, any size, number, and configuration of exhalation holes 122 which function as described is suitable and contemplated within the scope of the present invention.

In various embodiments, the air tube 115 is also attached to an air supply tube 125. Preferably, this is a removable attachment. Optionally, the connection at a second attachment point 130 between the air tube 115 and the air supply tube 125 also allows rotation while maintaining a leak-proof connection. Ideally, 360 degrees of rotation is enabled. In certain embodiments, the air tube 115 is bent somewhere along its length, such that the planes of rotation at the two attachment points 120 and 130 are different planes of rotation. For example, if the air tube is bent by about 90 degrees, the planes of rotation will be substantially orthogonal with respect to one another. In some embodiments, one plane of rotation will be parallel to the face of the user, and the other will be perpendicular to the user. This allows for a great degree of freedom of movement of the user without compromising the integrity of the seal formed between the device and the user's nostrils.

In various embodiments, the device includes at least one nostril interface tube 135 having an internal passage extending from the interface body 105 to the nostrils of a user. Preferably, there are two such tubes or nostril interface elements 135 extending to the nostrils of a user. In certain embodiments, the nostril interface elements 135 include an upper cushion 140, which is a radial protrusion, preferably formed of compressible material such that the upper surface of the cushion can be compressed against the outer edge of the nostril to help form a seal with the nostril of the user. Ideally, nostril interface tubes 135 are each formed as a single integral piece which can be attached and removed from the interface body 105.

Preferably, the nostril interface elements 135 also include a lower radial element 145 which is a radial protrusion adapted to be urged toward the upper cushion 140 and to compress the upper cushion 140 to aid in forming a seal between the upper cushion 140 and a person's nostril when the device 100 is warn by a person. In certain embodiments, the lower radial element 145 includes an internal substantially rigid rim 152 adapted to aid in compressing the upper cushion 140 when the device 100 is warn by a person.

Ideally, the nostril interface elements 135 have substantially non-porous surfaces. For example, they may be formed entirely of a non-porous material such as silicone or any other suitable material. Alternatively, at least the exposed surfaces of the nostril interface elements 135 are coated with a non-porous material such as silicone, or any other suitable material. In certain embodiments, the nostril interface elements 135 are removably attached to the interface body 105, such as via a snap fit, frictional fit, threading, or any other suitable method. Thus, they can be removed for cleaning or replacement.

The device 100 includes a facial patch 150. The facial patch can be adhered to the face of a user. Preferably, the facial patch 150 is a nose cover 150 which adheres to the nose of a user. The nose cover 150 preferably includes an adhesive on its bottom surface to removably adhere to the skin of the user's nose. The adhesive is ideally suitable for use on skin and removable. This nose cover 150 is ideally disposable and replaceable.

The nose cover 150 is ideally formed of a flexible material. Optionally, a bendable element 155 is included as part of the nose cover 150 which may be embedded within it or on one of its surfaces. The bendable element 155 is formed of a material which can be bent to fit the contour of the nose and hold its shape so as to help the nose cover 150 adhere to the nose. The bendable element may be formed of any suitable material, such as a metal as aluminum, or any other material with suitable properties.

In various embodiments, in order to hold the device 100 in place properly, at least one attachment flap 160, and preferably two attachment flaps 160 are connected to the nasal interface body 105. They secure to the surface of the nose cover 150. Any suitable manner of removable attachment is contemplated. For example, hook and loop attachment in which one element of the hook and loop material 165 is attached to the flaps 160, and the other element of the hook and loop material 170 is attached to the surface of the nose cover 150. However, an adhesive or other manner of attachment can be used. Ideally, the flaps 160 extend around the sides of the interface body 105 and hold the device 100 snug against the nostrils. In this way, no straps around the head of the user are required.

Figure 8:
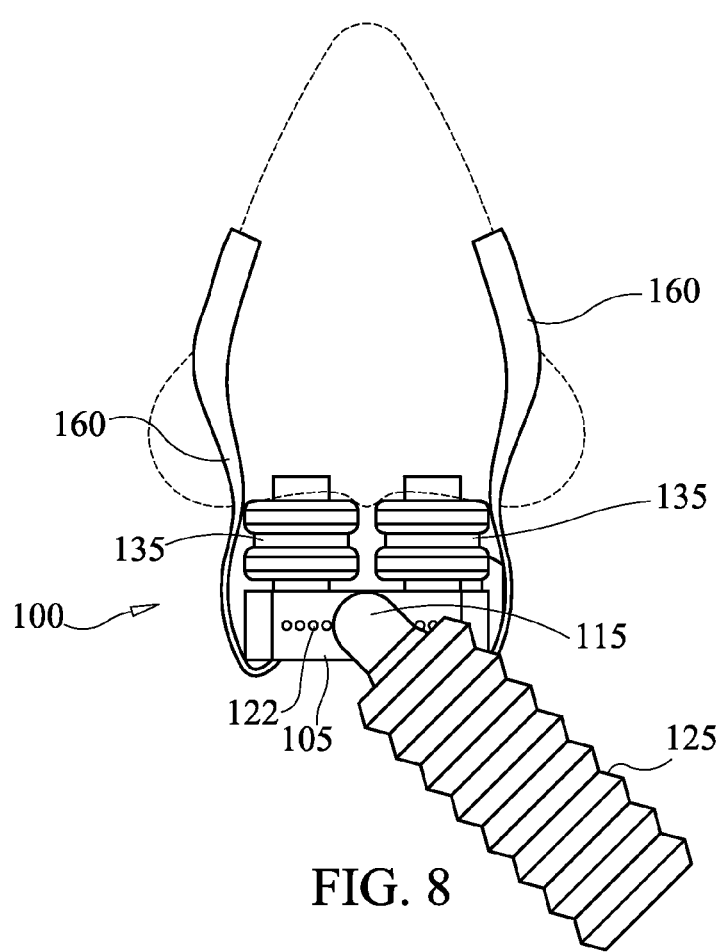
FIG. 8 shows another embodiment of the nasal interface device of the present invention.

In an alternate embodiment, the nostril interface elements 135 may include a magnet or iron or nickel bearing material, and they may be secured to the nose via magnets on the external surface of the nose. In a further alternate embodiment, as shown in FIG. 8, the nose cover 150 may be eliminated and one or more flaps 160 may be adhered directly to the outer surface of the nose of the user.

While specific embodiments have been illustrated and described, numerous modifications come to mind without significantly departing from the spirit of the invention and the scope of protection is limited by the scope of the accompanying claims.

What is claimed is:

1. A strapless nasal interface device comprising:
   an interface body having a cavity therein, said cavity having a passageway to an air tube extending from said interface body,
   at least one nostril interface tube having an internal passage extending from said interface body,
   a facial patch which is adherable to a portion of a person's face above the level of such a person's nostrils, and
   at least one attachment flap connected to said interface body and removably attachable to a surface of said facial patch above the level of such a person's nostrils adapted to hold said nostril interface tube in a secure position in which it communicates with a person's nostril when said facial patch is worn by such a person on the person's face and said attachment flap is attached to the surface of said facial patch in an operable mode, and wherein in said operable mode a seal sufficient for CPAP operation is formed between said nostril interface tube and a person's nostril.

2. The strapless nasal interface device according to claim 1, wherein said air tube is rotatably attached to said interface body via a first point of attachment which is substantially leak-proof regardless of a degree of rotation of said air tube.

3. The strapless nasal interface device according to claim 2, wherein said air tube is free to rotate 360 degrees at said first point of attachment.

4. The strapless nasal interface device according to claim 3, wherein said air tube is further removably and rotatably attachable to an air supply tube at a second point of attachment, and wherein said second point of attachment is substantially leak-proof regardless of a degree of rotation of said air tube with respect to said supply tube, wherein said air tube is bent along its length, and wherein rotation at said first point of attachment can occur in a plane which is different from a plane of rotation at said second point of attachment.

5. The strapless nasal interface device according to claim 1, wherein said at least one nostril interface tube comprises two nostril interface elements, and wherein said nostril interface elements each comprise an upper cushion comprising a radial protrusion and having an upper surface adapted to interface with the outside edge of a person's nostril.

6. The strapless nasal interface device according to claim 5, wherein said upper cushion comprises a compressible material.

7. The strapless nasal interface device according to claim 6, wherein said nostril interface elements further comprise a lower radial element comprising a radial protrusion adapted to be urged toward said upper cushion and to compress said upper cushion to aid in forming a seal between said upper cushion and a person's nostril when said device is worn by a person.

8. The strapless nasal interface device according to claim 7, wherein said lower radial element comprises an internal substantially rigid rim adapted to aid in compressing said upper cushion when said device is worn by a person.

9. The strapless nasal interface device according to claim 6, wherein said nostril interface elements are removably attachable to said interface body, and wherein said nostril interface elements comprise substantially non-porous surfaces.

10. The strapless nasal interface device according to claim 9, wherein at least said substantially non-porous surfaces comprise a silicone material.

11. The strapless nasal interface device according to claim 1, wherein said facial patch is a nose cover having an adhesive on a bottom surface adapted to removably adhere to the outer surface of a person's nose.

12. The strapless nasal interface device according to claim 11, wherein said at least one attachment flap comprises two attachment flaps each connected at one end to said interface body and removably attachable to said nose cover.

13. The strapless nasal interface device according to claim 12, wherein said attachment flaps are each removably attachable to said nose cover via hook and loop fasteners having opposing elements disposed on a surface of said attachment flaps and on a surface of said nose cover.

14. The strapless nasal interface device according to claim 12, wherein said attachment flaps extend on opposing sides of said interface body.

15. The strapless nasal interface device according to claim 11, wherein said nose cover comprises a bendable element adapted to be bent to match contours of a person's nose and hold its shape.

16. The strapless nasal interface device according to claim 1, wherein said interface body further comprises at least one exhalation hole adapted to allow exhaled air to pass therethrough without substantially depressurizing the cavity.

17. A strapless nasal interface device comprising:
   an interface body having a cavity therein, said cavity having a passageway to an air tube extending from said interface body,
   at least one nostril interface tube having an internal passage extending from said interface body, and
   at least one attachment flap connected to said interface body and removably attachable to a surface of the nose of a user and adapted to hold said nostril interface tube in a position in which it communicates with a person's nostril when said attachment flap is attached to the surface of the nose of a user in an operable mode, and wherein in said operable mode a seal sufficient for CPAP operation is formed between said nostril interface tube and a person's nostril.

18. A strapless nasal interface device comprising:

an interface body having a cavity therein, said cavity having a passageway to an air tube extending from said body, at least one nostril interface tube having an internal passage extending from said interface body, a compressible expandable nasal interface element disposed on an exterior of said nostril interface tube, wherein said nasal interface element is compressible to fit within a nostril of a user and expandable to make contact with the skin at the inner edge of the nostril to hold said interface tube in place within the nostril.

19. The strapless nasal interface device according to claim 18, wherein said nasal interface element is removable from said nostril interface tube and disposable, and wherein said nasal interface element comprises mounting means on an inner surface to removably mount said element to said nostril interface tube.

20. The strapless nasal interface device according to claim 18, further comprising a pair of side flaps each extending from a side of said interface body, the distal ends of which have an adhesive thereon to mount to the exterior of the nose of a user to assist in securing said device.

* * * * *